United States Patent [19]

Wu et al.

[11] Patent Number: 6,046,371
[45] Date of Patent: Apr. 4, 2000

[54] SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO OLEFINS

[75] Inventors: An-hsiang Wu; Ralph Melton, both of Bartlesville; Charles A. Drake, Nowata, all of Okla.

[73] Assignee: Phillips Petroleum Company, Bartlesville, Okla.

[21] Appl. No.: 09/305,400

[22] Filed: May 5, 1999

[51] Int. Cl.⁷ .............................. C07C 1/00; B01J 27/182
[52] U.S. Cl. ........................ 585/638; 585/639; 585/640; 502/208; 502/214; 502/232; 502/240; 502/263
[58] Field of Search ...................................... 502/208, 214, 502/232, 240, 263; 585/638, 639, 640

[56] References Cited

U.S. PATENT DOCUMENTS

| | | | |
|---|---|---|---|
| 4,440,871 | 4/1984 | Lok et al. | 502/214 |
| 5,126,308 | 6/1992 | Barger et al. | 502/214 |
| 5,185,310 | 2/1993 | Degnan et al. | 502/214 |
| 5,248,647 | 9/1993 | Barger | 502/214 |
| 5,475,182 | 12/1995 | Janssen | 585/640 |
| 5,663,471 | 9/1997 | Kvisle et al. | 585/639 |

OTHER PUBLICATIONS

Catalyst Deactivation 1997: Proceedings of International Symposium, Cancun, Mexico, Oct. 1997 (Elsevier Science), "The Role of Coke Deposition in the Conversion of Methanol to Olefins over SAPO–34", De Chen et al., pp. 159–166.

Copending Application S.N. 09/262,799 filed Mar. 4, 1999.

*Primary Examiner*—Elizabeth D. Wood
*Attorney, Agent, or Firm*—Jeffrey R. Anderson

[57] ABSTRACT

A catalyst system comprising a silylated silicoaluminophosphate composition, and methods of preparing such catalyst system, are disclosed. The thus-obtained catalyst system is employed as a catalyst in the conversion of a hydrocarbon feedstock comprising oxygenated hydrocarbons to olefins.

55 Claims, No Drawings

1

SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO OLEFINS

BACKGROUND OF THE INVENTION

The invention relates to catalyst systems useful in hydrocarbon upgrading processes and to methods for their production and use. In another aspect, this invention relates to processes for converting oxygenated hydrocarbons to $C_2$–$C_4$ olefins with an increase in olefin selectivity and a reduction in coke formation resulting from the conversion of such oxygenated hydrocarbons in the presence of such catalyst systems.

The term "oxygenated hydrocarbons" as employed herein comprises hydrocarbons containing aliphatic moieties such as, but not limited to, alcohols, halides, mercaptans, sulfides, amines, ethers, and carbonyl compounds (aldehydes, ketones, carboxylic acids and the like) or mixtures thereof.

It is known to convert oxygenated hydrocarbons to olefins in the presence of catalysts which contain a silicoaluminophosphate (SAPO), as is described in U.S. Pat. Nos. 4,861,938; 5,475,182; 5,248,647 and 5,663,471, the disclosures of each incorporated herein by reference.

One concern with the use of SAPO catalysts in the conversion of oxygenated hydrocarbons to olefins is the excessive production of coke during the conversion reaction. Coke formed during the SAPO catalyzed conversion of oxygenated hydrocarbons tends to cause catalyst deactivation. It is desirable to improve processes for the conversion of oxygenated hydrocarbons to olefins by minimizing the amount of coke formed during such processes. It is also desirable to have a SAPO catalyst that is useful in producing significant quantities of olefin conversion products.

SUMMARY OF THE INVENTION

It is an object of this invention to provide an improved SAPO material which when used in the conversion of oxygenated hydrocarbons results in increased olefin yield and decreased coke production.

A yet further object of this invention is to provide a method for making an improved SAPO material having such desirable properties as providing for increased olefin yield and decreased coke production when used in the conversion of oxygenated hydrocarbons.

Another object of this invention is to provide an improved process for the conversion of oxygenated hydrocarbons in which the yield of olefins is increased and the production of coke is decreased.

The inventive catalyst system comprises a silylated SAPO composition. The inventive catalyst system can be prepared by silylating a SAPO under suitable conditions. The inventive catalyst system can be used in the conversion of an oxygenated hydrocarbon to olefins by contacting, under conversion conditions, a hydrocarbon feedstock comprising at least one oxygenated hydrocarbon with the inventive catalyst system.

Other objects and advantages of the invention will become apparent from the detailed description and the appended claims.

DETAILED DESCRIPTION OF THE INVENTION

As used herein, the term "silylated silicoaluminophosphate composition" is defined as a silicoaluminophosphate that has had incorporated thereon or impregnated therein a silylating agent.

The SAPO material used in preparing the inventive catalyst system can be any SAPO that is effective in the conversion of oxygenated hydrocarbons to olefins when contacted under conversion conditions with oxygenated hydrocarbons.

SAPO catalysts exhibit properties of both aluminosilicate zeolites and aluminophosphates. The SAPO's have a three-dimensional microporous crystal framework structure of $PO_2$, $AlO_2$ and $SiO_2$ tetrahedral units. The chemical composition (anhydrous) is:

mR: $(Si_xAl_yP_z)O_2$ wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y" and "z" represent the mole fractions of silicon, aluminum and phosphorus, respectively.

Examples of such templating agents include, but are not limited to, tetramethylammonium hydroxide, tetraethylammonium hydroxide, and tetrapropylammonium hydroxide. Further details relating to the formation of SAPO compositions, including molar amounts of each oxide source, can be found in the Lok et al. U.S. Pat. No. 4,440,871, the entire disclosure of which is expressly incorporated herein by reference.

SAPO compositions useful in the present invention include, but are not limited to, SAPO-4, SAPO-5, SAPO-11, SAPO- 16, SAPO-17, SAPO-20, SAPO-31, SAPO-34, SAPO-35, SAPO-37, SAPO-40, SAPO-41, SAPO-42, and SAPO-44. The presently more preferred SAPO is SAPO-34.

According to a first embodiment of the present invention, the silylated SAPO composition can be prepared by the following method.

Generally, the SAPO is calcined prior to further treatment to produce a calcined SAPO. The calcination temperature is generally in the range of from about 250° C. to about 1000° C., preferably from about 350° C. to about 750° C., and most preferably from 450° C. to 650° C. and a pressure in the range of from about 0.5 to about 50 atmospheres (atm), preferably from about 0.5 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours. It will be understood that the foregoing calcination conditions are equally applicable to subsequent calcination steps performed in the preparation of the compositions of the first embodiment of the present invention.

The thus produced calcined SAPO can be silylated by any suitable means or method known in the art for silylating SAPOs to form a silylated calcined SAPO. A presently preferred method is to contact the calcined SAPO with a silylating agent under conditions suitable for silylating SAPOs.

The silylating agent can be any suitable silicon containing compound that effectively treats the calcined SAPO so as to provide a silylated calcined SAPO that is effective in giving a low rate of coke formation when used in converting oxygenated hydrocarbons to olefins. More particularly, the silylating agent is an organosilicon compound selected from the group consisting of compounds defined by the formulas:

$SiR_yX_{4-y}$, $(R_wX_{3-w}Si)_2 \cdot Z$, $[SiR_mOX_{2-m}]_n$, $[SiR_mX_{2-m}]_n$ and combinations of any two or more thereof, wherein:
y=1 to 4;
w=1 to 3;
m=1 to 2;
n>2, preferably>5, and most preferably in the range of from 10 to 5,000,000;
R=alkyl, aryl, H, alkoxy, arylalkyl;
X=halide; and
Z=oxygen or imino or alkylimino or alkanoylimino.

The presently preferred silylating agent is selected from the group consisting of tetraalkyl orthosilicates and poly (alkylaryl) siloxanes. The most preferred silylating agents are those selected from the group consisting of tetraethyl orthosilicate and poly (methylphenyl) siloxane.

The preferred silylating method is to impregnate the calcined SAPO with a solution of the silylating agent by any suitable standard incipient wetness technique known in the art. The solution may be an aqueous solution or a hydrocarbon solution of the silylating agent. It is preferred, however, for the silylating agent to be insoluble in water but soluble in hydrocarbon. Any suitable hydrocarbon solvent can be used including, for example, aromatics and other hydrocarbons having from 4 to 10 carbon atoms per molecule including alkanes, cycloalkanes and olefins. The most preferred hydrocarbon solvent is cyclohexane. The concentration of silylating agent in the solution can generally range upwardly to the solubility limit of the silylating agent in the solvent. Preferably, the concentration of the silylating agent in the solution can be in the range of from about 1 weight percent to about 99 weight percent. Most preferred, the concentration of silylating agent in the solvent is from 5 to 25 weight percent.

The weight ratio of the silylating agent in the solution to the SAPO material (e.g. calcined SAPO) impregnated is preferably in the range of from about 0.01:1 to about 2:1, more preferably from about 0.05:1 to about 1:1, and most preferably from 0.1:1 to 0.5:1.

It will be understood that the foregoing silylation conditions are equally applicable to the subsequent silylation step performed in the preparation of the compositions of the first embodiment of the present invention.

After the incorporation of silylating agent into the calcined SAPO, the thus produced silylated calcined SAPO can be dried at suitable drying conditions, generally in the presence of air, and then calcined to form a calcined silylated calcined SAPO. The drying conditions generally include a temperature in the range of from about 20° C. to about 125° C. and a time period in the range of from about 0.1 hour to about 4 hours. The calcination conditions are the same as those described above for the initial calcination of SAPO prior to further treatment.

The calcined silylated calcined SAPO can be combined or mixed with a binder material, to thereby form a mixture, in a liquid such as water or a hydrocarbon, by any means known to one skilled in the art such as stirring, blending, kneading, or extrusion, following which the resulting mixture can be dried in air at a temperature in the range of from about 20° C. to about 125° C., for a time period in the range of from about 0.1 hour to about 4 hours under any pressures that accommodate the temperatures, preferably atmospheric pressure.

Any binders known to one skilled in the art for use with a SAPO are suitable for use herein. Examples of suitable binders include, but are not limited to, aluminas such as for example α-alumina and γ-alumina; silicas; alumina-silica; aluminum phosphate; aluminum chlorohydrate; clays such as kaolinite, halloysite, vermiculite, chlorite, attapulgite, smectite, montmorillonite, illite, saconite, sepiolite, palygorskite, and combinations of any two or more thereof. Because these binders are well known to one skilled in the art, description of which is omitted herein. The presently preferred binder is silica.

The mixture can be extruded into pellets or tablets by any method known to those skilled in the art.

Generally, the mixture is calcined prior to further treatment to form a calcined mixture. Preferably, the calcination conditions are the same as those described above for the initial calcination of SAPO prior to further treatment.

It has been unexpectedly found that the treatment of the calcined mixture described above with a silylating agent, as further described above, provides a catalyst system having improved catalytic properties. In particular, the silylated calcined mixture provides a catalyst which yields a low rate of coke formation when used in the conversion of hydrocarbons in comparison to such calcined mixture that has not been treated with a silylating agent.

The calcined mixture can be silylated by the same silylation method described above for the initial silylation of the calcined SAPO.

The thus produced silylated calcined mixture can be dried, as described above for drying the silylated calcined SAPO, and calcined under conditions suitable for producing the silylated SAPO composition. Preferably, the calcination conditions are the same as those described above for the initial calcination of SAPO prior to further treatment.

The amount of silicon, from silylating the calcined SAPO and from silylating the calcined mixture, incorporated into the silylated SAPO composition should be such as to provide a silylated material that effectively provides a suitably high production of olefins with a low rate of coke formation during its use in the conversion of oxygenated hydrocarbons to olefins.

According to a second embodiment of the present invention, the silylated SAPO composition can be prepared by the following method.

The SAPO, as described above, can be combined or mixed with a binder material, as described above, to thereby form a mixture, in a liquid such as water or a hydrocarbon, by any means known to one skilled in the art such as stirring, blending, or kneading, following which the resulting mixture can be extruded into pellets or tablets by any method known to those skilled in the art. The resulting mixture, whether or not extruded, can be dried in air at a temperature in the range of from about 20° C. to about 125° C., for a time period in the range of from about 0.1 hour to about 4 hours under any pressures that accommodate the temperatures, preferably atmospheric pressure.

The mixture can be calcined prior to further treatment to thereby form a calcined mixture. The calcination temperature is generally in the range of from about 250° C. to about 1000° C., preferably from about 350° C. to about 750° C., and most preferably from 450° C. to 650° C. and a pressure in the range of from about 0.5 to about 50 atmospheres (atm), preferably from about 0.5 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours. It will be understood that the foregoing calcination conditions are equally applicable to subsequent calcination steps performed in the preparation of the compositions of the second embodiment of the present invention.

The calcined mixture can be silylated by any suitable means or method known in the art for silylating SAPOs to form a silylated calcined mixture. A presently preferred method is to contact the calcined mixture with a silylating agent, as described above, under conditions suitable for silylating SAPOs.

The preferred silylating method is to impregnate the calcined mixture with a solution of the silylating agent by any suitable standard incipient wetness technique known in the art. The solution may be an aqueous solution or a hydrocarbon solution of the silylating agent. It is preferred, however, for the silylating agent to be insoluble in water but soluble in hydrocarbon. Any suitable hydrocarbon solvent can be used including, for example, aromatics and other hydrocarbons having from 4 to 10 carbon atoms per molecule including alkanes, cycloalkanes and olefins. The most preferred hydrocarbon solvent is cyclohexane. The concentration of silylating agent in the solution can range upwardly to the solubility limit of the silylating agent in the solvent. Preferably, the concentration of the silylating agent in the solution can be in the range of from about 1 weight percent to about 99 weight percent. Most preferred, the concentration of silylating agent in the solvent is from 5 to 25 weight percent.

The weight ratio of the silylating agent in the solution to the SAPO material (e.g. the SAPO material contained in the calcined mixture) impregnated is preferably in the range of from about 0.01:1 to about 2:1, more preferably from about 0.05:1 to about 1:1, and most preferably from 0.1:1 to 0.5:1.

It will be understood that the foregoing silylation conditions are equally applicable to the subsequent silylation step performed in the preparation of the compositions of the second embodiment of the present invention.

After the incorporation of silylating agent into the calcined mixture, the resulting silylated calcined mixture can be dried, as described above for drying the resulting mixture of the second embodiment of the present invention, and then calcined to form a calcined silylated calcined mixture. The calcination conditions are preferably the same as those described above for the calcination of the mixture of the second embodiment of the present invention.

It has been unexpectedly found that the treatment of the calcined silylated calcined mixture described above with a silylating agent, as described above, provides a catalyst system having improved catalytic properties. In particular, the silylated calcined silylated calcined mixture provides a catalyst which yields a low rate of coke formation when used in the conversion of hydrocarbons in comparison to such calcined silylated calcined mixture that has not been treated with a silylating agent.

The calcined silylated calcined mixture can be silylated by the same silylation method described above for silylation of the calcined mixture of the second embodiment of the present invention to form a silylated calcined silylated calcined mixture.

The silylated calcined silylated calcined mixture can be dried, as described above for drying the resulting mixture of the second embodiment of the present invention, and calcined under conditions suitable for producing the silylated SAPO composition. Preferably, the calcination conditions are the same as those described above for the calcination of the mixture of the second embodiment of the present invention.

The amount of silicon, from silylating the calcined mixture and from silylating the calcined silylated calcined mixture, incorporated into the silylated SAPO composition should be such as to provide a silylated material that effectively provides a suitably high production of olefins with a low rate of coke formation during its use in the conversion of oxygenated hydrocarbons to olefins.

Any suitable hydrocarbon feedstock, which comprises at least one oxygenated hydrocarbon, can be used as the feed to be contacted with the inventive catalyst system under suitable process conditions for obtaining a reaction product comprising olefins. The aliphatic moieties of the oxygenated hydrocarbons preferably contain in the range of from about 1 to about 10 carbon atoms, and more preferably, contain from about 1 to about 4 carbon atoms. Representative oxygenated hydrocarbons include, but are not limited to, lower straight or branched chain alcohols, their unsaturated counterparts and the nitrogen, halogen and sulfur analogues of such. Examples of suitable compounds include, but are not limited to, methanol, isopropanol; n-propanol; ethanol; fuel alcohols; methyl mercaptan, methyl sulfide; methyl amine, dimethyl ether; ethyl mercaptan; ethyl chloride; diethyl ether; methylethyl ether;

formaldehyde; dimethyl ketone; acetic acid; n-alkyl amines; n-alkyl halides and n-alkyl sulfides having n-alkyl groups of 3 to 10 carbon atoms; and mixtures of any two or more thereof. The preferred oxygenated hydrocarbon is methanol.

The hydrocarbon feedstock can be contacted, by any suitable manner, with the inventive catalyst system described herein contained within a reaction zone. The contacting step can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The contacting step is preferably carried out within a conversion reaction zone, wherein is contained the inventive catalyst system, and under reaction conditions that suitably promote the formation of olefins, preferably light olefins, from at least a portion of the oxygenated hydrocarbons of the hydrocarbon feedstock. The reaction temperature of the contacting step is more particularly in the range of from about 200° C. to about 800° C., preferably from about 250° C. to about 750° C. and, most preferably, from 300° C. to 700° C. The contacting pressure can range from subatmospheric pressure upwardly to about 500 psig, preferably, from about atmospheric pressure to about 450 psig and, most preferably, from atmospheric pressure to 400 psig.

The flow rate at which the hydrocarbon feedstock is charged to the conversion reaction zone is such as to provide a weight hourly space velocity ("WHSV") in the range of from exceeding 0 hour$^{-1}$ upwardly to about 1000 hour$^{-1}$. The term "weight hourly space velocity", as used herein, shall mean the numerical ratio of the rate at which a hydrocarbon feedstock is charged to the conversion reaction zone in pounds per hour divided by the pounds of catalyst contained in the conversion reaction zone to which the hydrocarbon is charged. The preferred WHSV of the feed to the conversion reaction zone or contacting zone can be in the range of from about 0.25 hour$^{-1}$ to about 250 hour$^{-1}$ and, most preferably, from 0.5 hours$^{-1}$ to 100 hour$^{-1}$.

The olefin production process is generally carried out in the presence of one or more inert diluents which can be present in an amount in the range of from about 1 to about 99 molar percent, based on the total number of moles of all feed and diluent components fed to the reaction zone. Suitable diluents include, but are not limited to, helium, argon, nitrogen, carbon monoxide, carbon dioxide, hydrogen, water, paraffins, hydrocarbons (such as methane and the like), aromatic compounds, and mixtures of any two or more thereof. The presently preferred diluent is water.

The following examples are presented to further illustrate this invention and are not to be construed as unduly limiting its scope.

EXAMPLE 1

This example illustrates the preparation of catalysts which were subsequently tested as catalysts in the conversion of a hydrocarbon feedstock comprising methanol to olefins.

Catalyst A (Control)

A 10 gram quantity of a commercially available SAPO-34 catalyst (provided by UOP, LLC, Des Plaines, Ill. under product designation SAPO-34) was mixed with a 10 gram quantity of a colloidal silica solution (manufactured by DuPont under product designation Ludox® AS-40). The formed mixture was then extruded into ¹⁄₁₆" diameter pellets and dried at room temperature followed by calcining at a temperature of about 538° C. for 6 hours.

Catalyst B (Control)

A 2 gram quantity of Catalyst A was impregnated, by incipient wetness, with a solution containing 0.4 gram of tetraethyl orthosilicate and 3.6 grams of cyclohexane. The thus-obtained impregnated material was dried at room temperature followed by calcining at a temperature of about 538° C. for 6 hours.

Catalyst C (Control)

A 10 gram quantity of a commercially available SAPO-34 catalyst (provided by UOP, LLC, Des Plaines, Ill. under product designation SAPO-34) was calcined at a temperature of about 538° C. for 3 hours. The thus calcined SAPO-34 was impregnated, by incipient wetness, with a solution containing 2 grams of tetraethyl orthosilicate and 18 grams of cyclohexane. The thus-obtained impregnated material was dried at room temperature followed by calcining at a temperature of about 538° C. for 6 hours. The thus-obtained calcined impregnated material was mixed with a 17.4 gram quantity of a colloidal silica solution (Ludox® AS-40 described above). The formed mixture was then extruded into ¹⁄₁₆" diameter pellets and dried at room temperature followed by calcining at a temperature of about 538° C. for 6 hours.

Catalyst D (Invention)

A 2 gram quantity of Catalyst C was impregnated, by incipient wetness, with a solution containing 0.4 gram of tetraethyl orthosilicate and 3.6 grams of cyclohexane. The thus-obtained impregnated material was dried at room temperature followed by calcining at a temperature of about 538° C. for 6 hours.

Catalyst E (Invention)

A quantity of a commercially available SAPO-34 catalyst (provided by UOP, LLC, Des Plaines, Ill. under product designation SAPO-34) was mixed with an equal quantity of a colloidal silica solution (manufactured by DuPont under product designation Ludox® AS-40). The formed mixture was then extruded into ¹⁄₁₆" diameter pellets and dried at room temperature followed by calcining at a temperature of about 538° C. for 1 hour. A 4.9 gram quantity of the calcined formed mixture was impregnated, by incipient wetness, with a solution containing 2.5 grams of poly (methylphenyl) siloxane and 7.5 grams of cyclohexane. The thus-obtained impregnated material was dried at room temperature followed by calcining at 538° C. for 6 hours.

Catalyst F (Invention)

A 3.05 gram quantity of Catalyst E was impregnated, by incipient wetness, with a solution containing 0.38 gram of poly(methylphenyl) siloxane and 1.12 grams of cyclohexane. The thus-obtained impregnated material was dried at room temperature followed by calcining at a temperature of about 538° C. for 6 hours.

EXAMPLE 2

This example illustrates the use of the catalysts described in Example 1 in the conversion of methanol to olefins.

In Run 1, a 2.32 gram quantity of Catalyst A described in Example 1 was placed into a stainless steel tube reactor (length: about 18 inches; inner diameter: about 0.5 inch). The steel reactor tube was heated to a temperature in the range of from about 450° C. to about 452° C. The reactor pressure was about 0 psig. A methanol/water feed, comprising 20 mole % methanol and 80 mole % water, was introduced to the reactor tube at a flow rate of 25 mL/hour to yield a methanol WHSV of 3.1. The product was analyzed by means of a gas chromatograph. Test data results obtained after 7.3 hours on stream are summarized in the Table.

In Run 2, a 1.81 gram quantity of Catalyst B described in Example 1 was placed into a stainless steel tube reactor (length: about 18 inches; inner diameter: about 0.5 inch). The steel reactor tube was heated to a temperature in the range of from about 445 ° C. to about 453° C. The reactor pressure was about 0 psig. A methanol/water feed, comprising 20 mole % methanol and 80 mole % water, was introduced to the reactor tube at a flow rate of 25 mL/hour to yield a methanol WHSV of 3.9. The product was analyzed by means of a gas chromatograph. Test data results obtained after 7.1 hours on stream are summarized in the Table.

In Run 3, a 1.89 gram quantity of Catalyst C described in Example 1 was placed into a stainless steel tube reactor (length: about 18 inches; inner diameter: about 0.5 inch). The steel reactor tube was heated to a temperature in the range of from about 448° C. to about 453° C. The reactor pressure was about 0 psig. A methanol/water feed, comprising 20 mole % methanol and 80 mole % water, was introduced to the reactor tube at a flow rate of 25 mL/hour to yield a methanol WHSV of 3.8. The product was analyzed by means of a gas chromatograph. Test data results obtained after 7.0 hours on stream are summarized in the Table.

In Run 4, a 1.99 gram quantity of Catalyst D described in Example 1 was placed into a stainless steel tube reactor (length: about 18 inches; inner diameter: about 0.5 inch). The steel reactor tube was heated to a temperature in the range of from about 449° C. to about 450° C. The reactor pressure was about 0 psig. A methanol/water feed, comprising 20 mole % methanol and 80 mole % water, was introduced to the reactor tube at a flow rate of 25 mL/hour to yield a methanol WHSV of 3.6. The product was analyzed by means of a gas chromatograph. Test data results obtained after 7.0 hours on stream are summarized in the Table.

In Run 5, a 2.49 gram quantity of Catalyst E described in Example 1 was placed into a stainless steel tube reactor (length: about 18 inches; inner diameter: about 0.5 inch). The steel reactor tube was heated to a temperature in the range of from about 448° C. to about 453° C. The reactor pressure was about 0 psig. A methanol/water feed, comprising 20 mole % methanol and 80 mole % water, was introduced to the reactor tube at a flow rate of 25 mL/hour to yield a methanol WHSV of 2.9. The product was analyzed by means of a gas chromatograph. Test data results obtained after 7.7 hours on stream are summarized in the Table.

In Run 6, a 2.52 gram quantity of Catalyst F described in Example 1 was placed into a stainless steel tube reactor (length: about 18 inches; inner diameter: about 0.5 inch). The steel reactor tube was heated to a temperature of about 450° C. The reactor pressure was about 0 psig. A methanol/water feed, comprising 20 mole % methanol and 80 mole % water, was introduced to the reactor tube at a flow rate of 25 mL/hour to yield a methanol WHSV of 2.8. The product was analyzed by means of a gas chromatograph. Test data results obtained after 7.5 hours on stream are summarized in the Table.

TABLE

| Run | Catalyst | Methanol Conversion Wt. % | $\Sigma\ C_2^=-C_4^=$ Selectivity[1] % | Coke[2] Wt. %/hour |
|---|---|---|---|---|
| 1 | A (Control) | 93.2 | 91.6 | 2.1 |
| 2 | B (Control) | 100 | 97.6 | 2.2 |
| 3 | C (Control) | 99.7 | 96.7 | 1.9 |
| 4 | D (Invention) | 100 | 98.6 | 1.0 |
| 5 | E (Invention) | 90.6 | 93.7 | 1.7 |
| 6 | F (Invention) | 92.9 | 96.6 | 0.7 |

[1] $\Sigma\ C_2^=-C_4^=$ Selectivity is defined as the weight % of $\Sigma\ C_2^=-C_4^=$ in the product divided by the weight % methanol conversion, multiplied by 100.
[2] Coke was determined at the end of the reaction by removing the catalysts from the reactor and measuring the coke with a thermal gravimetric analyzer (TGA), manufactured by TA Instruments, New Castle, Delaware.

The test data presented in the Table show that use of the inventive Catalyst D in Run 4 resulted in an increased $C_2^=$ to $C_4^=$ selectiviy and a considerable decrease in coke production as compared to the use of control Catalysts A, B and C in Runs 1, 2 and 3, respectively.

The test data presented in the Table also show that use of the inventive Catalysts E and F in Runs 5–6, respectively, resulted in a considerable decrease in coke production as compared to the use of control Catalysts A, B and C in Runs 1, 2 and 3, respectively.

Inventive Run 4 demonstrated an increase in $C_2^=$ to $C_4^=$ selectivity in the range of from 1% to 2% over control Runs 1–3; and a decrease in coke production in the range of from 33% to 55% over control Runs 1–3.

Inventive Run 5 demonstrated a decrease in coke production in the range of from 11% to 23% over control Runs 1–3.

Inventive Run 6 demonstrated a decrease in coke production in the range of from 63% to 68% over control Runs 1–3.

From the data in the Table, it is readily apparent that the inventive catalyst system results in increased olefin yield and decreased coke production when used in the conversion of oxygenated hydrocarbons, as compared to control Catalysts A, B and C.

Reasonable variations, modifications, and adaptations can be made within the scope of the disclosure and the appended claims without departing from the scope of this invention.

That which is claimed is:

1. A catalyst system comprising a silylated silicoaluminophosphate composition.

2. A catalyst system as recited in claim 1 wherein said silylated silicoaluminophosphate composition has been subjected to calcination.

3. A catalyst system as recited in claim 2 wherein said silylated silicoaluminophosphate composition has been calcined at a temperature in the range of from about 200° C. to about 1000° C. for a time period in the range of from about 0.1 hour to about 30 hours.

4. A catalyst system as recited in claim 1 wherein said silylated silicoaluminophosphate composition is prepared by contacting a silicoaluminophosphate with a silylating agent.

5. A catalyst system as recited in claim 4 wherein said silicoaluminophosphate is SAPO-34.

6. A catalyst system as recited in claim 4 wherein said silylating agent is an organosilicon compound selected from the group consisting of compounds defined by the formulas:

$$SiR_yX_{4-y},$$

$$(R_wX_{3-w}Si)_2\cdot Z,$$

$$[SiR_mOX_{2-m}]_n,$$

$$[SiR_mX_{2-m}]_n$$

and combinations of any two or more thereof, wherein:
y=1 to 4;
w=1 to 3;
m=1 to 2;
n>2;
R=alkyl, aryl, H, alkoxy, arylalkyl;
X=halide; and
Z=oxygen or imino or alkylimino or alkanoylimino.

7. A catalyst system as recited in claim 6 wherein said organosilicon compound is selected from the group consisting of tetraalkyl orthosilicates and poly(alkylaryl) siloxanes.

8. A catalyst system as recited in claim 4 wherein the weight ratio of said silylating agent, contacted with said silicoaluminophosphate, to said silicoaluminophosphate is in the range of from about 0.01:1 to about 2:1.

9. A catalyst system as recited in claim 1 wherein said silylated silicoaluminophosphate composition is prepared by the method of:

silylating a calcined silicoaluminophosphate thereby forming a silylated calcined silicoaluminophosphate;

calcining said silylated calcined silicoaluminophosphate thereby forming a calcined silylated calcined silicoaluminophosphate;

mixing said calcined silylated calcined silicoaluminophosphate with a binder thereby forming a mixture;

calcining said mixture thereby forming a calcined mixture;

silylating said calcined mixture thereby forming a silylated calcined mixture; and calcining said silylated calcined mixture thereby forming said silylated silicoaluminophosphate composition.

10. A catalyst system as recited in claim 9 wherein said calcined silicoaluminophosphate is calcined SAPO-34.

11. A catalyst system as recited in claim 9 wherein said binder is silica.

12. A catalyst system as recited in claim 9 wherein said calcined silicoaluminophosphate is prepared by calcining a silicoaluminophosphate.

13. A catalyst system as recited in claim 12 wherein said silicoaluminophosphate, said silylated calcined silicoaluminophosphate, said mixture and said silylated calcined mixture are calcined at a temperature in the range of from about 200° C. to about 1000° C. for a time period in the range of from about 0.1 hour to about 30 hours.

14. A catalyst system as recited in claim 9 wherein said step of silylating a calcined silicoaluminophosphate comprises contacting said calcined silicoaluminophosphate with a silylating agent.

15. A catalyst system as recited in claim 14 wherein said silylating agent is an organosilicon compound selected from the group consisting of compounds defined by the formulas:

$SiR_yX_{4-y}$, $(R_wX_{3-w}Si)_2 \cdot Z$, $[SiR_mOX_{2-m}]_n$, $[SiR_mX_{2-m}]_n$ and combinations of any two or more thereof, wherein:
y=1 to 4;
w=1 to 3;
m=1 to 2;
n>2;
R=alkyl, aryl; H, alkoxy, arylalkyl;
X=halide; and
Z=oxygen or imino or alkylimino or alkanoylimino.

16. A catalyst system as recited in claim 9 wherein said step of silylating a calcined silicoaluminophosphate comprises contacting said calcined silicoaluminophosphate with a solution containing an organosilicon compound; and wherein said organosilicon compound is selected from the group consisting of tetraalkyl orthosilicates, poly(alkylaryl) siloxanes and combinations of any two or more thereof.

17. A catalyst system as recited in claim 9 wherein said step of silylating said calcined mixture comprises contacting said calcined mixture with a silylating agent.

18. A catalyst system as recited in claim 17 wherein said silylating agent is an organosilicon compound selected from the group consisting of compounds defined by the formulas:

$SiR_yX_{4-y}$, $(R_wX_{3-w}Si)_2 \cdot Z$, $[SiR_mOX_{2-m}]_n$, $[SiR_mX_{2-m}]_n$ and combinations of any two or more thereof, wherein:
y=1 to 4;
w=1 to 3;
m=1 to 2;
n>2;
R=alkyl, aryl, H, alkoxy, arylalkyl;
X=halide; and
Z=oxygen or imino or alkylimino or alkanoylimino.

19. A catalyst system as recited in claim 9 wherein said step of silylating said calcined mixture comprises contacting said calcined mixture with a solution containing an organosilicon compound; and wherein said organosilicon compound is selected from the group consisting of tetraalkyl orthosilicates, poly(alkylaryl) siloxanes and combinations of any two or more thereof.

20. A catalyst system as recited in claim 9 wherein said mixture is extruded prior to calcining said mixture.

21. A catalyst system as recited in claim 14 wherein the weight ratio of said silylating agent, contacted with said calcined silicoaluminophosphate, to said calcined silicoaluminophosphate is in the range of from about 0.01:1 to about 2:1.

22. A catalyst system as recited in claim 17 wherein the weight ratio of said silylating agent, contacted with said calcined mixture, to said calcined mixture is in the range of from about 0.01:1 to about 2:1.

23. A catalyst system comprising a silylated silicoaluminophosphate composition prepared by the method of:
calcining a silicoaluminophosphate comprising SAPO-34 at a temperature in the range of from about 200° C. to about 1000° C. for a time period in the range of from about 0.1 hour to about 30 hours thereby forming a calcined silicoaluminophosphate;
silylating said calcined silicoaluminophosphate by contacting said calcined silicoaluminophosphate with a first solution comprising a silylating agent comprising an organosilicon compound selected from the group consisting of tetraalkyl orthosilicates, poly(alkylaryl) siloxanes, and combinations of any two or more thereof, thereby forming a silylated calcined silicoaluminophosphate;
calcining said silylated calcined silicoaluminophosphate at a temperature in the range of from about 200° C. to about 1000° C. for a time period in the range of from about 0.1 hour to about 30 hours thereby forming a calcined silylated calcined silicoaluminophosphate;
mixing said calcined silylated calcined silicoaluminophosphate with silica thereby forming a mixture;
extruding said mixture thereby forming an extruded mixture;
calcining said extruded mixture at a temperature in the range of from about 200° C. to about 1000° C. for a time period in the range of from about 0.1 hour to about 30 hours thereby forming a calcined extruded mixture;
silylating said calcined extruded mixture by contacting said calcined extruded mixture with a second solution comprising a silylating agent comprising an organosilicon compound selected from the group consisting of tetraalkyl orthosilicates, poly(alkylaryl) siloxanes, and combinations of any two or more thereof, thereby forming a silylated calcined extruded mixture;
calcining said silylated calcined extruded mixture at a temperature in the range of from about 200° C. to about 1000° C. for a time period in the range of from about 0.1 hour to about 30 hours thereby forming said silylated silicoaluminophosphate composition; and
wherein the weight ratio of said silylating agent of said first solution, contacted with said calcined silicoaluminophosphate, to said calcined silicoaluminophosphate is in the range of from about 0.01:1 to about 2:1, and the weight ratio of said silylating agent of said second solution, contacted with said calcined extruded mixture, to said calcined extruded mixture is in the range of from about 0.01:1 to about 2:1.

24. A catalyst system as recited in claim 1 wherein said silylated silicoaluminophosphate composition is prepared by the method of:
mixing a silicoaluminophosphate with a binder thereby forming a mixture;
calcining said mixture thereby forming a calcined mixture;
silylating said calcined mixture thereby forming a silylated calcined mixture;
calcining said silylated calcined mixture thereby forming a calcined silylated calcined mixture;

silylating said calcined silylated calcined mixture thereby forming a silylated calcined silylated calcined mixture; and calcining said silylated calcined silylated calcined mixture thereby forming said silylated silicoaluminophosphate composition.

25. A catalyst system as recited in claim 24 wherein said silicoaluminophosphate is SAPO-34.

26. A catalyst system as recited in claim 24 wherein said binder is silica.

27. A catalyst system as recited in claim 24 wherein said mixture, said silylated calcined mixture, and said silylated calcined silylated calcined mixture are each calcined at a temperature in the range of from about 200° C. to about 1000° C. for a time period in the range of from about 0.1 hour to about 30 hours.

28. A catalyst system as recited in claim 24 wherein said step of silylating said calcined mixture comprises contacting said calcined mixture with a silylating agent.

29. A catalyst as recited in claim 28 wherein said silylating agent is an organosilicon compound selected from the group consisting of compounds defined by the formulas:

$$SiR_yX_{4-y},$$

$$(R_wX_{3-w}Si)_2 \cdot Z,$$

$$[SiR_mOX_{2-m}]_n,$$

$$[SiR_mX_{2-m}]_n$$

and combinations of any two or more thereof, wherein:

y=1 to 4;
w=1 to 3;
m=1 to 2;
n>2;
R=alkyl, aryl, H, alkoxy, arylalkyl;
X=halide; and
Z=oxygen or imino or alkylimino or alkanoylimino.

30. A catalyst system as recited in claim 24 wherein said step of silylating said calcined mixture comprises contacting said calcined mixture with a solution containing an organosilicon compound; and wherein said organosilicon compound is selected from the group consisting of tetraalkyl orthosilicates, poly(alkylaryl) siloxanes and combinations of any two or more thereof.

31. A catalyst system as recited in claim 24 wherein said step of silylating said calcined silylated calcined mixture comprises contacting said calcined silylated calcined mixture with a silylating agent.

32. A catalyst system as recited in claim 31 wherein said silylating agent is an organosilicon compound selected from the group consisting of compounds defined by the formulas:

$$SiR_yX_{4-y},$$

$$(R_wX_{3-w}Si)_2 \cdot Z,$$

$$[SiR_mOX_{2-m}]_n,$$

$$[SiR_mX_{2-m}]_n$$

and combinations of any two or more thereof, wherein:

y=1 to 4;
w=1 to 3;
m=1 to 2;
n>2;
R=alkyl, aryl, H, alkoxy, arylalkyl;
X=halide; and
Z=oxygen or imino or alkylimino or alkanoylimino.

33. A catalyst system as recited in claim 24 wherein said step of silylating said calcined silylated calcined mixture comprises contacting said calcined silylated calcined mixture with a solution containing an organosilicon compound; and wherein said organosilicon compound is selected from the group consisting of tetraalkyl orthosilicates, poly (alkylaryl) siloxanes and combinations of any two or more thereof.

34. A catalyst system as recited in claim 24 wherein said mixture is extruded prior to calcining said mixture.

35. A catalyst system as recited in claim 28 wherein the weight ratio of said silylating agent, contacted with said calcined mixture, to said calcined mixture is in the range of from about 0.01:1 to about 2:1.

36. A catalyst system as recited in claim 31 wherein the weight ratio of said silylating agent, contacted with said calcined silylated calcined mixture, to said calcined silylated calcined mixture is in the range of from about 0.01:1 to about 2:1.

37. A catalyst system comprising a silylated silicoaluminophosphate composition prepared by the method of:

mixing a silicoaluminophosphate with silica thereby forming a mixture;

extruding said mixture thereby forming an extruded mixture;

calcining said extruded mixture at a temperature in the range of from about 200° C. to about 1000° C. for a time period in the range of from about 0.1 hour to about 30 hours thereby forming a calcined extruded mixture;

silylating said calcined extruded mixture by contacting said calcined extruded mixture with a first solution comprising a silylating agent comprising an organosilicon compound selected from the group consisting of tetraalkyl orthosilicates, poly(alkylaryl) siloxanes and combinations of any two or more thereof, thereby forming a silylated calcined extruded mixture;

calcining said silylated calcined extruded mixture at a temperature in the range of from about 200° C. to about 1000° C. for a time period in the range of from about 0.1 hour to about 30 hours thereby forming a calcined silylated calcined extruded mixture;

silylating said calcined silylated calcined extruded mixture by contacting said calcined silylated calcined extruded mixture with a second solution comprising a silylating agent comprising an organosilicon compound selected from the group consisting of tetraalkyl orthosilicates, poly(alkylaryl) siloxanes, and combinations of any two or more thereof, thereby forming a silylated calcined silylated calcined extruded mixture;

calcining said silylated calcined silylated calcined extruded mixture at a temperature in the range of from about 200° C. to about 1000° C. for a time period in the range of from about 0.1 hour to about 30 hours thereby forming said silylated silicoaluminophosphate composition; and wherein the weight ratio of said silylating agent of said first solution, contacted with said calcined extruded mixture, to said calcined extruded mixture is in the range of from about 0.01:1 to about 2:1, and the weight ratio of said silylating agent of said second solution, contacted with said calcined silylated calcined extruded mixture, to said calcined silylated calcined extruded mixture is in the range of from about 0.01:1 to about 2:1.

38. A method of preparing a catalyst system comprising a silylated silicoaluminophosphate composition which comprises the steps of:

(a) silylating a silicoaluminophosphate thereby forming a silylated silicoaluminophosphate; and (b) calcining said silylated silicoaluminophosphate thereby forming said silylated silicoaluminophosphate composition.

39. A method in accordance with claim 38 wherein said silicoaluminophosphate is SAPO-34.

40. A method in accordance with claim 38 wherein said step (a) comprises contacting said silicoaluminophosphate with a silylating agent.

41. A method in accordance with claim 40 wherein said silylating agent is an organosilicon compound selected from the group consisting of compounds defined by the formulas:

$$SiR_yX_{4-y},$$

$$(R_wX_{3-w}Si)_2 \cdot Z,$$

$$[SiR_mOX_{2-m}]_n,$$

$$[SiR_mX_{2-m}]_n$$

and combinations of any two or more thereof, wherein:

y=1 to 4;

w=1 to 3;

m=1 to 2;

n>2;

R=alkyl, aryl, H, alkoxy, arylalkyl;

X=halide; and

Z=oxygen or imino or alkylimino or alkanoylimino.

42. A method in accordance with claim 41 wherein said organosilicon compound is selected from the group consisting of tetraalykl orthosilicates, poly(alkylaryl) siloxanes, and combinations of any two or more thereof.

43. A method in accordance with claim 38 wherein said calcining of said silylated silicoaluminophosphate is conducted at a temperature in the range of from about 200° C. to about 1000° C. for a time period in the range of from about 0.1 hour to about 30 hours.

44. A process for converting at least a portion of a hydrocarbon feedstock comprising at least one oxygenated hydrocarbon to at least one olefin which comprises contacting said hydrocarbon feedstock at conversion conditions with the catalyst system of claim 1.

45. A process as recited in claim 44 wherein said conversion conditions include a temperature in the range of from about 200° C. to about 800° C., a pressure in the range of from about 0 psig to about 1000 psig, and a weight hourly space velocity in the range of from about 0.01 hour$^{-1}$ to about 1000 hours$^{-1}$.

46. A process as recited in claim 44 wherein said at least one oxygenated hydrocarbon comprises methanol.

47. A process for converting at least a portion of a hydrocarbon feedstock comprising at least one oxygenated hydrocarbon to at least one olefin which comprises contacting said hydrocarbon feedstock at conversion conditions with the catalyst system of claim 9.

48. A process as recited in claim 47 wherein said conversion conditions include a temperature in the range of from about 200° C. to about 800° C., a pressure in the range of from about 0 psig to about 1000 psig, and a weight hourly space velocity in the range of from about 0.01 hour$^{-1}$ to about 1000 hours$^{-1}$.

49. A process as recited in claim 47 wherein said at least one oxygenated hydrocarbon comprises methanol.

50. A process for converting at least a portion of a hydrocarbon feedstock comprising at least one oxygenated hydrocarbon to at least one olefin which comprises contacting said hydrocarbon feedstock at conversion conditions with the catalyst system of claim 24.

51. A process as recited in claim 50 wherein said conversion conditions include a temperature in the range of from about 200° C. to about 800° C., a pressure in the range of from about 0 psig to about 1000 psig, and a weight hourly space velocity in the range of from about 0.01 hours$^{-1}$ to about 1000 hours$^{-1}$.

52. A process as recited in claim 50 wherein said at least one oxygenated hydrocarbon comprises methanol.

53. A process for converting at least a portion of a hydrocarbon feedstock comprising at least one oxygenated hydrocarbon to at least one olefin which comprises contacting said hydrocarbon feedstock at conversion conditions with a catalyst system prepared by the method of claim 38.

54. A process as recited in claim 53 wherein said conversion conditions include a temperature in the range of from about 200° C. to about 800° C., a pressure in the range of from about 0 psig to about 1000 psig, and a weight hourly space velocity in the range of from about 0.01 hour$^{-1}$ to about 1000 hours$^{-1}$.

55. A process as recited in claim 53 wherein said at least one oxygenated hydrocarbon comprises methanol.

* * * * *

UNITED STATES PATENT AND TRADEMARK OFFICE
CERTIFICATE OF CORRECTION

PATENT NO. : 6,046,371
DATED : April 4, 2000
INVENTOR(S) : An-hsiang Wu, Ralph Melton, and Charles A. Drake It is certified that error appears in the above-indentified patent and that said Letters Patent is hereby corrected as shown below:

Claim 15, line 24, delete ";" after aryl and insert - - - , - - - therefor.

Signed and Sealed this

Twentieth Day of March, 2001

Attest:

NICHOLAS P. GODICI

*Attesting Officer*  *Acting Director of the United States Patent and Trademark Office*